United States Patent
Thorne et al.

(10) Patent No.: US 8,845,668 B2
(45) Date of Patent: Sep. 30, 2014

(54) ARTHROSCOPIC SHAVER HANDPIECE WITH MODULAR ATTACHMENTS

(75) Inventors: Marc Thorne, Oldsmar, FL (US); Jonh Sieh, Safe Harbor, FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 13/586,259

(22) Filed: Aug. 15, 2012

(65) Prior Publication Data

US 2012/0316591 A1 Dec. 13, 2012

Related U.S. Application Data

(63) Continuation of application No. 11/392,820, filed on Mar. 29, 2006, now abandoned.

(60) Provisional application No. 60/680,670, filed on May 13, 2005, provisional application No. 60/706,581, filed on Aug. 9, 2005.

(51) Int. Cl.
*A61B 17/32* (2006.01)
*A61B 17/16* (2006.01)
*A61B 17/3207* (2006.01)
*A61B 17/00* (2006.01)

(52) U.S. Cl.
CPC ..... *A61B 17/320783* (2013.01); *A61B 17/1622* (2013.01); *A61B 17/1624* (2013.01); *A61B 2017/00473* (2013.01); *A61B 2017/00469* (2013.01); *A61B 17/32002* (2013.01); *A61B 17/1633* (2013.01)
USPC ...................................................... 606/180

(58) Field of Classification Search
USPC ........ 433/91–96; 606/32, 34, 42, 79–80, 159, 606/1, 167, 172–180
See application file for complete search history.

(56) References Cited

U.S. PATENT DOCUMENTS

| | | | | |
|---|---|---|---|---|
| 3,384,085 A * | 5/1968 | Hall | | 606/180 |
| 3,582,097 A * | 6/1971 | Elliott, Jr. | | 279/61 |
| 3,584,629 A * | 6/1971 | Hoef et al. | | 606/180 |
| 4,705,038 A * | 11/1987 | Sjostrom et al. | | 606/180 |
| 5,112,299 A * | 5/1992 | Pascaloff | | 604/22 |
| 5,122,134 A * | 6/1992 | Borzone et al. | | 606/80 |
| 5,178,605 A * | 1/1993 | Imonti | | 604/22 |
| 5,269,794 A * | 12/1993 | Rexroth | | 606/180 |
| RE34,556 E * | 3/1994 | Sjostrom et al. | | 606/170 |
| 5,391,144 A * | 2/1995 | Sakurai et al. | | 604/22 |
| 5,993,454 A * | 11/1999 | Longo | | 606/80 |
| 6,017,354 A * | 1/2000 | Culp et al. | | 606/170 |
| 6,050,989 A * | 4/2000 | Fox et al. | | 606/1 |
| 6,059,719 A * | 5/2000 | Yamamoto et al. | | 600/127 |
| 6,090,123 A * | 7/2000 | Culp et al. | | 606/180 |
| 6,152,941 A * | 11/2000 | Himes et al. | | 606/180 |
| 6,159,209 A * | 12/2000 | Hakky | | 606/45 |
| 6,464,711 B1 * | 10/2002 | Emans et al. | | 606/167 |
| 6,500,169 B1 * | 12/2002 | Deng | | 606/1 |
| 8,475,441 B2 * | 7/2013 | Babkin et al. | | 606/21 |
| 2002/0087179 A1 * | 7/2002 | Culp et al. | | 606/167 |
| 2003/0229351 A1 * | 12/2003 | Tidwell et al. | | 606/80 |
| 2004/0133189 A1 * | 7/2004 | Sakurai | | 606/1 |
| 2004/0138687 A1 * | 7/2004 | Himes | | 606/167 |
| 2004/0147934 A1 * | 7/2004 | Kiester | | 606/80 |
| 2004/0201183 A1 * | 10/2004 | Burdette | | 279/62 |
| 2005/0090848 A1 * | 4/2005 | Adams | | 606/180 |
| 2005/0090849 A1 * | 4/2005 | Adams | | 606/180 |
| 2005/0159767 A1 * | 7/2005 | Adams et al. | | 606/180 |
| 2005/0256512 A1 * | 11/2005 | Del Rio et al. | | 606/1 |
| 2009/0105740 A1 * | 4/2009 | Lee et al. | | 606/177 |
| 2011/0208170 A1 * | 8/2011 | Hafner et al. | | 606/1 |

* cited by examiner

*Primary Examiner* — David Eastwood

(57) ABSTRACT

An apparatus, system and method are presented by which certain surgical procedures normally done by powered surgical handpieces may be accomplished by powered arthroscopic handpieces, thus obviating the need to use powered surgical handpieces.

12 Claims, 3 Drawing Sheets

ARTHROSCOPIC SHAVER HANDPIECE WITH MODULAR ATTACHMENTS

CROSS-REFERENCE TO RELATED APPLICATIONS

This application is a continuation U.S. Non-provisional patent application Ser. No. 11/392,820 filed Mar. 29, 2006 and claims the benefit of U.S. Provisional Application No. 60/680,670, filed May 13, 2005 and U.S. Provisional Application No. 60/706,581, filed Aug. 9, 2005.

FIELD OF THE INVENTION

The invention relates to powered handpieces and attachments used to perform surgical procedures.

BACKGROUND

Surgical procedures are often performed using instruments attached to handpieces which are powered either electrically or pneumatically. Powered handpieces generally fall into two groups: powered surgical handpieces and powered arthroscopic/endoscopic handpieces.

Powered surgical handpieces are generally used in open surgical procedures and have bodies in the form of pistol grip or pencil grip type structures. These bodies move a variety of instruments (e.g. saws, drills, reamers, pins, wires, etc.) attachable to the bodies in order to treat tissue during a surgical procedure. Each of the instruments has a distal working end which actually performs a function (e.g. sawing, drilling, reaming, etc.) and a proximal connecting end which enables the instrument to be attached to the handpiece providing the motive force. The movements are generally in the form of oscillating, rotating, or reciprocating movements of the instruments. A variety of instruments may be directly secured to the drive motor in the body of the handpiece or a common handpiece may have a variety of attachments interposed between the body and the instrument such that the same body may, by simply changing the attachments, create a variety of motions to the instrument (e.g. oscillation, rotation, reciprocation).

One type of powered surgical handpiece includes pin drivers and wire drivers. This type of handpiece includes a pistol grip and has a cannulated shaft transversely attached to the pistol grip. The shaft has a bore extending completely through it and is adapted to receive and grip an elongated pin or wire. The bore is designed to coaxially receive a range of diameters of pins/wires. A selectively actuated chuck grips the pin/wire which can then be rotated about the axis of the bore to drive the distal tip of the pin/wire into a bore. The grip can be released to enable the handpiece to be either removed or repositioned to drive the pin/wire further into the bone.

Powered arthroscopic/endoscopic handpieces are generally used in closed surgical procedures and have bodies in the form of pencil type structures which, in the current state of the art, are generally electrically powered to operate shaver blades or burs secured to the distal end of the handpiece. These handpieces will be referred to as arthroscopic handpieces throughout this specification. The term "arthroscopic" as used herein is intended to broadly include endoscopic devices and procedures in general. Shaver blades generally include a stationary tubular outer member having a cutting window situated at its distal end and a rotatable tubular inner member also having a cutting window situated at its distal end. The inner and outer members are sometimes referred to individually and collectively as shaver blades. Either of the cutting windows may be formed in a variety of shapes and may or may not include teeth depending upon the degree of aggressiveness desired and the particular surgical procedure for which the shaver blade is designed. Rotation of the inner member within the outer member causes the resection of any tissue which penetrates into the lumen of the inner member as it rotates. The lumen of the inner member is at its proximal end attached to a vacuum in order to aspirate the resected tissue as well as irrigation fluid and other tissue which may be at the surgical site. Powered arthroscopic handpieces are generally used during arthroscopic procedures in which the surgical site is commonly inflated with fluid in order to provide distention and visibility to imaging instruments also at the surgical site. It will also be understood that an arthroscopic handpiece, modified in accordance with the teachings of this invention, could also be used in open surgical procedures.

It is often necessary to use a powered surgical handpiece in the same procedure as an arthroscopic handpiece, thus requiring two separate powered handpieces to be prepared and presented for use.

SUMMARY

The subject invention relates to an apparatus, system and method by which certain surgical procedures normally done by powered surgical handpieces may be accomplished by powered arthroscopic handpieces, thus obviating the need to use powered surgical handpieces.

The subject invention also relates to an apparatus, system and method by which pin and/or wire driving surgical procedures normally done by dedicated powered surgical handpieces may be accomplished by powered arthroscopic shaver handpieces, thus obviating the need to use powered surgical handpieces.

The subject invention also relates to an apparatus, system and method by which a pencil grip type arthroscopic handpiece may be easily converted to a pistol grip type handpiece.

BRIEF DESCRIPTION OF THE DRAWINGS

Various examples of the present invention will be discussed with reference to the appended drawings. These drawings depict only illustrative examples of the invention and are not to be considered limiting of its scope. The drawings including individual figures in which.

DETAILED DESCRIPTION

Figure 1:
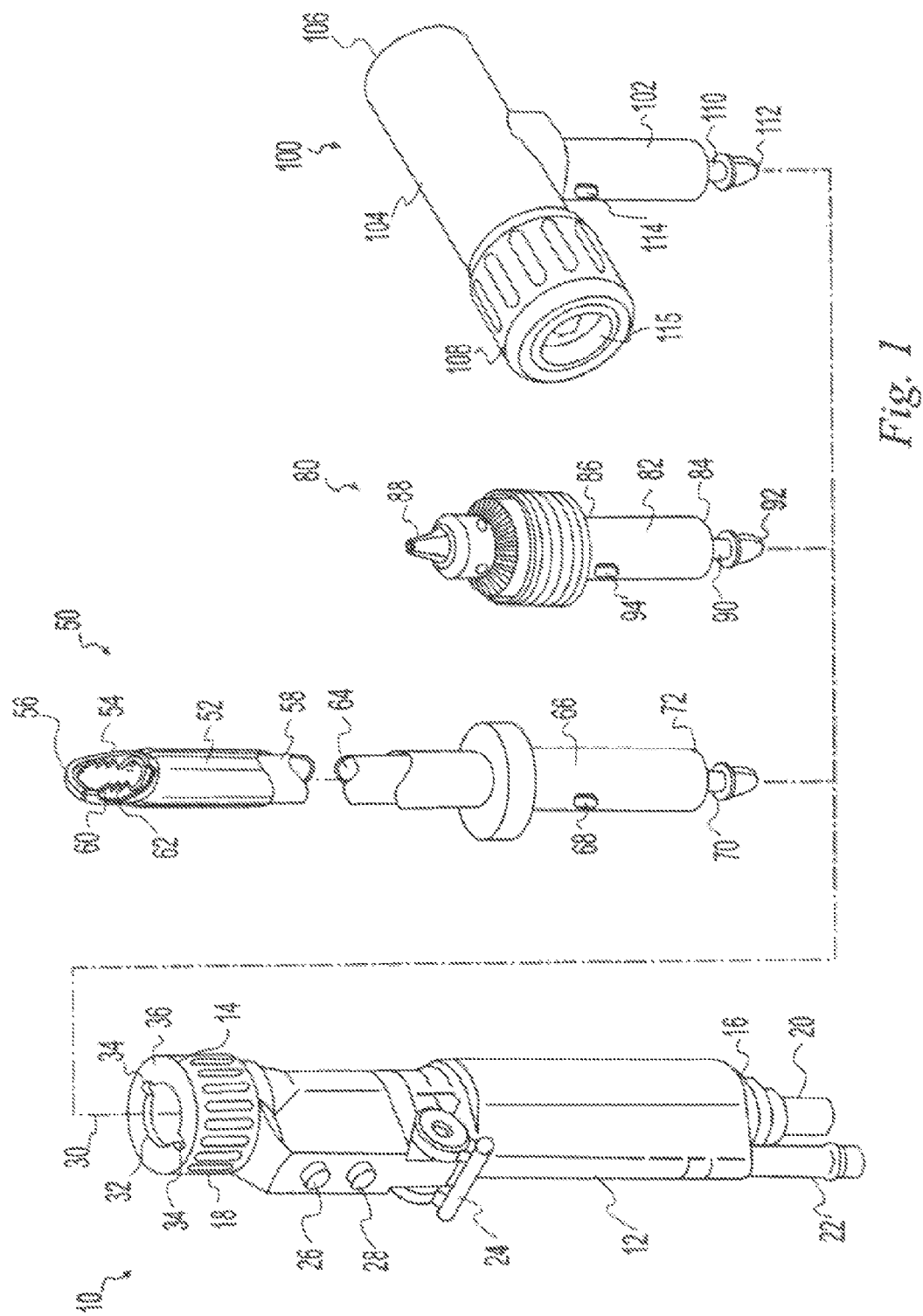
FIG. 1 is an exploded perspective view of an arthroscopic shaver handpiece and modular attachments according to the present invention.

As shown in FIG. 1, a conventional arthroscopic handpiece 10 includes a body 12, a distal end 14, a proximal end 16, and a collet 18. The handpiece 10 also includes at its proximal end 14 a power cord 20 and a vacuum tube 22. The vacuum tube 22 is joined by an internal channel (not shown) to the distal end 14 of the handpiece 10. A vacuum control lever 24 controls the degree of vacuum applied through the internal channel to the distal end 14. The arthroscopic handpiece 10 includes a motor and drive shaft (not shown), which motor is operated by a control system (not shown) and controlled by control buttons 26 and 28. The drive shaft rotates about an axis 30. Modular attachments are inserted through an opening 32 in the collet 18 to engage the drive shaft. By rotating the collet 18, opposed keyways 34 are aligned with internal grooves (not shown) to receive or release corresponding keys formed on the modular attachments. When fully inserted into the collet 18, the modular attachments will engage the motor drive shaft and will be retained by rotation of the collet 18 about the axis 30 to trap the keys behind the front flange 36 of the collet 18.

An arthroscopic shaver blade 50 includes a stationary tubular outer member 52 having a cutting window 54 situated at its distal end 56 and a rotatable tubular inner member 58 also having a cutting window 60 situated at its distal end. The illustrative inner member 58 includes optional teeth 62 for aiding in gripping and cutting tissue at a surgical site. Rotation of the inner member 58 within the outer member 52 resects tissue which penetrates into the lumen 64 of the inner member 58 as it rotates. The inner and outer members 58, 52 are mounted to a housing 66 which is mountable to the arthroscopic handpiece 10. The housing 66 is sized to fit through the opening 32 in the collet 18 of the handpiece 10 and includes a radially extending key 68 engageable with the keyways 34 of the collet 18. The inner member 58 is connected to a drive shaft 70 that extends through the housing 66 to engage the motor drive shaft of the arthroscopic handpiece 10. The lumen 64 of the inner member 58 communicates with the proximal end 72 of the housing which in turn communicates with the inner channel and vacuum tube 22 of the arthroscopic handpiece 10. Tissue resected by the shaver blade 50 and irrigation fluid are aspirated from the surgical site through the vacuum tube 22. The arthroscopic handpiece 10 may similarly be used with a bur (not shown) with an annular vacuum channel as is known in the art.

A variety of modular attachments may be substituted for the shaver blade 50 to convert the arthroscopic handpiece to surgical handpiece applications. For example, FIG. 1 illustrates a Jacobs chuck assembly 80 which serves as a drive shaft extension and adapter able to receive in its distal end a variety of instruments which would not otherwise be able to be operated by the arthroscopic handpiece 10. The assembly includes a housing 82 having a proximal end 84 and a distal end 86 to which is secured a distal chuck 88. The housing 82 contains a drivable shaft 90 and other components adapted to operatively connect the shaft 90 to the distal chuck 88. The drivable shaft 90 has a proximal end 92 configured to be operatively engaged with the motor drive shaft in the arthroscopic handpiece 10. In the preferred embodiment, the motor drive shaft is rotatable about the axis 30 of the handpiece 10. The diameter of the housing 82 is sized to be received within the opening 32 of the collet 18. The exterior surface of housing 82 is provided with a radially extending key 94 adapted to be received through either of the diametrically opposed keyways 34 in the collet 18. When so assembled, the Jacobs chuck assembly 80 may be operated in a conventional manner to attach selected instruments such as drill bits, reamers, drivers, etc. so that the handpiece 10 may be used like a drill rather than a shaver. In addition to the convenience of being able to drive powered surgical instruments with an arthroscopic handpiece, for certain procedures, the ability to use a pencil type grip may enhance the ergonomics over the use of a pistol grip powered surgical handpiece.

FIG. 1 also illustrates a transverse attachment 100 for the arthroscopic handpiece 10. The transverse attachment 100 includes a longitudinal housing 102 and a transverse body 104, having a proximal end 106 and a distal end 108 to which may be secured another attachment or instrument. The transverse attachment 100 contains a drivable shaft 110 and other drive transmission components adapted to operatively and transversely connect it and the arthroscopic handpiece 10 to an attachment or instrument. The drivable shaft 110 has a proximal end 112 configured to be operatively engaged with the motor drive shaft in the arthroscopic handpiece 10. As with the other illustrative attachments of FIG. 1, the longitudinal housing is adapted to be received within the circular opening 32 of the collet 18 and includes a radially extending key 114. The transverse attachment 100 includes a collet 115 which may be engaged directly with an instrument (such as a drill bit, reamer, saw blade, etc.) to drive the instrument or which may be engaged with another, intermediate attachment (such as a chuck, adapter, wire driver, reciprocating saw drive, oscillating saw drive, etc.) that is engaged with an instrument.

Figures 2, 3:
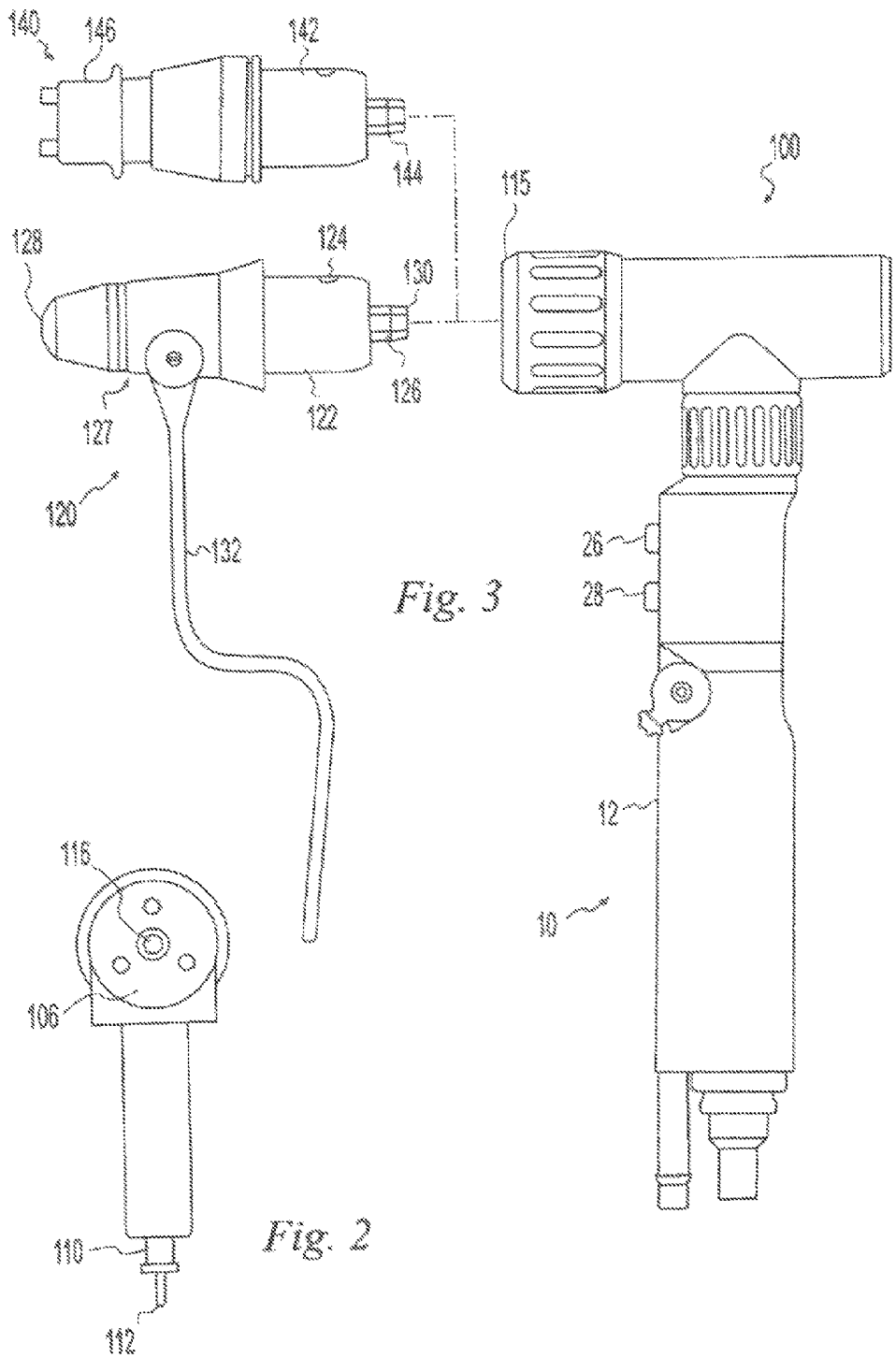
FIG. 2 is a side elevation view of one of the attachments of FIG. 1.
FIG. 3 is an exploded front elevation view of the handpiece of FIG. 1 assembled with one of the attachments of FIG. 1 and shown with additional modular attachments.

The transverse attachment 100 may be cannulated to accommodate a wire or pin driver and to permit use with cannulated drill bits that are driven over a guide wire. As seen in FIG. 2, the transverse attachment 100 may include a throughbore 116 extending from the proximal end 106 to the distal end 108 and through the collet 115 for receiving pins, wires, guide wires, etc.

FIG. 3, illustrates alternative modular attachments for use with the transverse attachment 100 including a wire driver 120 and a rotary instrument driver 140. The wire driver 120 includes a housing 122 and drivable shaft 126 compatible with the collet 115 of the transverse attachment 100. In the illustrative wire driver, the housing 122 is locked in the collet 115 by way of a locking detent 124 that receives a ball (not shown) in the collet 115. The wire driver 120 further includes an internal wire collet (not shown) mounted in the wire driver body 127. The wire collet communicates with the distal end 128 and is connected to the drivable shaft 126. A longitudinal through bore extends from the distal end 128 to the proximal end 130 through the wire collet and the drivable shaft 126 to communicate with the through bore 116 of the transverse attachment. An actuator 132 is operably connected to the wire chuck and pivots relative to the wire driver body 127. When the wire driver 120 is mounted in the transverse attachment 100, the actuator 132 is positioned adjacent the body 12 of the arthroscopic handpiece 10 convenient to the control buttons 26, 28 in pistol grip fashion. The actuator 132 may be operated to cause the wire chuck to selectively grip and release a wire. When the wire is gripped, the shaft 126 can be driven to rotate the wire about the axis of the bore 116 to drive the distal tip of the wire into a surgical site. When the wire is released, the wire driver 120 can be removed or repositioned to drive the wire further into the surgical site.

The rotary instrument driver 140 of FIG. 3 includes a housing 142 and drive shaft 144 compatible with the collet 115 of the transverse attachment 100. The driver shaft 144 connects to a distal drive collet 146 adapted to receive an instrument normally associated with powered surgical handpieces. Thus, the rotary instrument driver 140 converts the collet 115 of the transverse attachment 100 to a different style collet 146 to adapt the transverse attachment for use with different instruments.

While the transverse attachment 100 has been illustrated in use with two different attachments, any number of attachments and instruments may be used with the transverse attachment 100 including, by way of example only, drill attachments, saw attachments, wire and pin driver attachments, etc.

The transverse attachment 100 also serves to convert the pencil grip style arthroscopic handpiece 10 into a pistol grip style handpiece. For certain procedures the use of a pistol grip style handpiece may have enhanced ergonomics over the use of a pencil grip powered handpiece. For example, for drilling pilot holes, it may be desirable to engage the transverse attachment 100 with the arthroscopic handpiece 10 to convert it to a pistol grip style and then engage a drill bit drive attachment with the transverse attachment.

Figure 4:
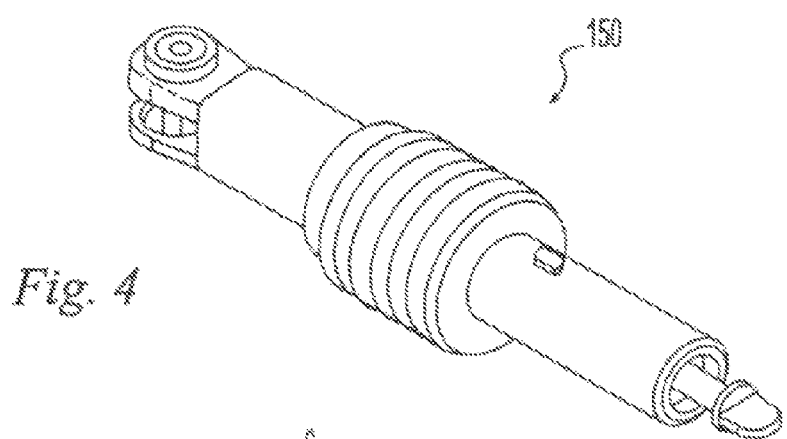
FIGS. 4 and 5 are perspective views of additional modular attachments for use with the handpiece of FIG. 1.

FIG. 4 illustrates an exemplary sagittal saw attachment 150 adapted to engage the arthroscopic handpiece 10 and convert it from shaver operation to sagittal saw operation.

Figure 5:
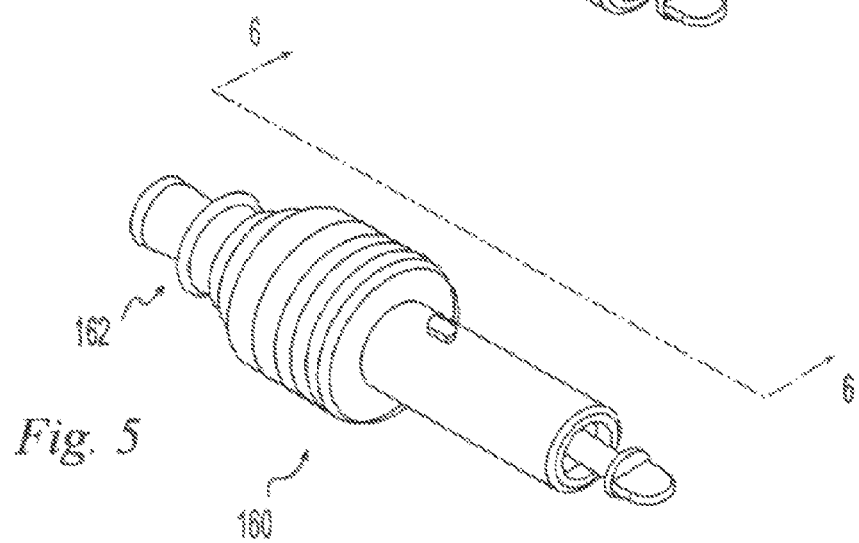

FIG. 5 illustrates an exemplary rotary instrument driver attachment 160 with a quick connect chuck 162 for rapidly connecting and disconnecting various rotary instruments generally associated with powered surgical handpieces.

Figure 6:
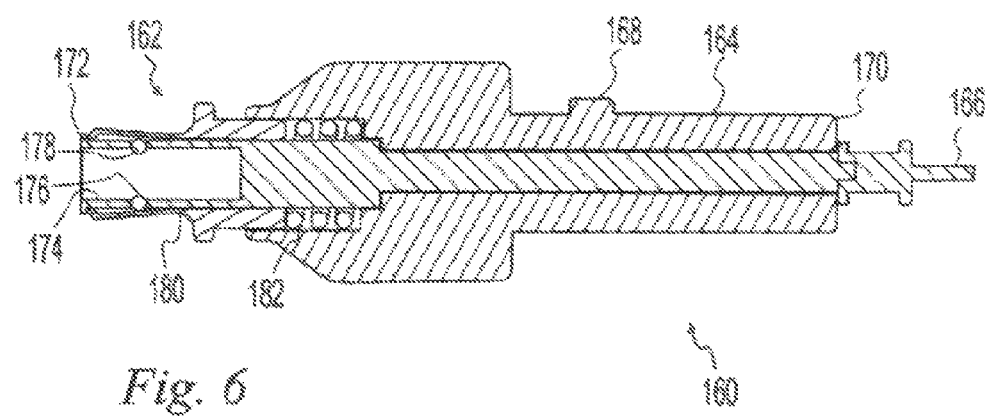
FIG. 6 is a cross sectional view taken along line 6-6 of FIG. 5.

FIG. 6 illustrates the inner mechanism of the attachment 160. The attachment includes a housing 164, drivable shaft 166, and key 168 similar to the attachments of FIG. 1. The drivable shaft 166 extends through the attachment from the proximal end 170 to the distal end 172 and defines an instrument receiving bore 174 in the quick connect chuck 162 at the distal end 172. One or more locking balls 176 are disposed in transverse bores 178 communicating with the instrument receiving bore 174. An outer sleeve 180 surrounds the drive shaft 166 at the distal end 172 and is mounted for axial translation along the drive shaft 166 between a first position in which the sleeve 180 presses the locking balls 176 into the instrument receiving bore 174 and a second position spaced from the locking balls 176. A spring 182 biases the sleeve 180 toward the first position. Moving the sleeve proximally against spring tension allows the balls 176 to move away from the instrument receiving bore 174 to admit or release an instrument, while allowing the spring 182 to bias the sleeve 180 distally causes the sleeve 180 to engage the balls 176 and lock the instrument in place.

The illustrative attachments may be driven directly from the motor in the arthroscopic handpiece 10 or they may be geared up or down by appropriate components in the attachments in order to alter the output speed and torque from that provided by the motor. The gear ratio may be different for different attachments in order to obtain the speed and torque required for each attachment.

The attachments may also include a variety of identification systems (e.g. magnets, radiofrequency identification "RFID" devices or chips, Hall sensors, optical devices, etc.) in order to convey information to the handpiece and the control system so that appropriate signals may be generated by the control system to optimize the use of the attachments for certain procedures requiring varying speeds and torques. The signals may also alter the operation of the handpiece buttons (e.g. toggle, momentary on/off, etc.).

The attachments may be variously configured for a variety of instruments such as a reciprocating saw for a reciprocating saw attachment, a sagittal saw for a sagittal saw attachment, assorted drills, reamers, pins, taps, screw drivers, etc. for rotary drive attachments, and any other suitable instruments. The instrument driven by the attachment may be a fixed integral part of the attachment or it may be modular and releasably attachable to the distal end of the attachment via a chuck, collet, and/or other mechanism.

It will be understood that the novel attachments described above inherently produce a novel arthroscopic system and novel method for performing surgery. It will be understood that during a normal arthroscopic surgery an arthroscopic shaver (or bur) will be used during certain portions of the procedure. Depending upon the procedure, at some point the need may arise for a powered surgical handpiece and its associated instrument (drill, reamer, coring reamer, saw, pin, wire, etc.) such that the use of the arthroscopic shaver must be discontinued and a portion of the procedure must be continued with the powered surgical handpiece. With the present invention, the surgeon may simply remove the arthroscopic shaver from the surgical site at a selected point in the procedure and replace the shaver blade with one of the attachments described above. The attachment may have an instrument already secured to it or an instrument or additional attachment may need to be attached to the attachment as described above. The surgery may then continue with the now modified arthroscopic shaver handpiece, thus obviating the need to prepare, sterilize, or use any powered surgical handpiece. Clearly the use of the powered arthroscopic handpiece and the arthroscopic handpiece/attachment assembly may be alternated as necessary during the procedure.

Although examples of attachments for arthroscopic shaver handpieces and their use have been described and illustrated in detail, it is to be understood that the same is intended by way of illustration and example only and is not to be taken by way of limitation. Accordingly, variations in and modifications to the attachments for arthroscopic shaver handpieces and their use will be apparent to those of ordinary skill in the art, and the following claims are intended to cover all such modifications and equivalents.

What is claimed is:

1. A method of performing an arthroscopic surgical procedure comprising the steps of:
providing a vacuum enabled arthroscopic shaver handpiece, a shaver blade and a modular attachment comprising a drill chuck;
attaching the shaver blade to the handpiece and using the handpiece to run the shaver blade during a first predetermined portion of the surgical procedure;
replacing the shaver blade with the modular attachment comprising the drill chuck by removing the shaver blade from the handpiece and attaching the modular attachment to the handpiece;
using the handpiece to run the modular attachment during a second predetermined portion of the surgical procedure.

2. The method of claim 1 wherein said handpiece comprises a pencil grip style, which is a generally cylindrical body having a pencil grip portion encircling a longitudinal axis, the generally cylindrical body extending between a distal end of said handpiece and a proximal end of said handpiece; a motor drive shaft extending along said longitudinal axis; a vacuum tube at said proximal end; a vacuum control lever operable to control a degree of vacuum applied to said distal end; and motor control buttons positioned on said generally cylindrical body between said distal end and said vacuum control lever.

3. The method of claim 2 wherein the modular attachment comprises a housing having a distal end, a proximal end, and a longitudinal axis extending a length of the housing through said proximal end of said housing and said distal end of said housing, said proximal end being adapted to be received within an opening defined by the distal end of said handpiece such that when said housing is connected to said handpiece, said longitudinal axis of said housing aligns with said longitudinal axis of said handpiece and a portion of said longitudinal axis of said housing is encircled by said pencil grip.

4. The method of claim 3 wherein the drill chuck is secured to said distal end of said housing such that said drill chuck remains secured to said housing when said modular attachment is disconnected from and separated from said handpiece, said drill chuck serving as an adapter to receive a connecting end of an instrument in a distal end thereof.

5. The method of claim 4 further comprising the step of operatively connecting a drivable shaft to said drill chuck, said drivable shaft extending though at least a portion of said housing, said drivable shaft remaining operatively connected to said drill chuck when said modular attachment is disconnected from and separated from said handpiece, and said drivable shaft having a proximal end configured to operatively engage said motor drive shaft.

6. The method of claim 4 further comprising the step of attaching said instrument to said drill chuck.

7. A method of performing an arthroscopic surgical procedure comprising the steps of:
- providing a vacuum enabled arthroscopic shaver handpiece;
- providing a shaver blade, attaching the shaver blade to the handpiece and using the handpiece to run the shaver blade during a predetermined portion of the surgical procedure;
- removing the shaver blade from the handpiece;
- providing a transverse attachment;
- attaching the transverse attachment to the handpiece;
- providing a modular attachment comprising a drill chuck;
- attaching the modular attachment to the transverse attachment to run the modular attachment at a working axis that is 90 degrees from a longitudinal axis of said handpiece during a predetermined portion of the surgical procedure.

8. The method of claim 7 wherein said handpiece comprises a pencil grip style, which is a generally cylindrical body having a pencil grip portion encircling a longitudinal axis, the generally cylindrical body extending between a distal end of said handpiece and a proximal end of said handpiece; a motor drive shaft extending along said longitudinal axis; a vacuum tube at said proximal end; a vacuum control lever operable to control a degree of vacuum applied to said distal end; and motor control buttons positioned on said generally cylindrical body between said distal end and said vacuum control lever.

9. The method of claim 8 wherein the modular attachment comprises a housing having a distal end, a proximal end, and a longitudinal axis extending a length of the housing through said proximal end of said housing and said distal end of said housing, said proximal end being adapted to be received within an opening defined by the distal end of said handpiece such that when said housing is connected to said handpiece, said longitudinal axis of said housing aligns with said longitudinal axis of said handpiece and a portion of said longitudinal axis of said housing is encircled by said pencil grip.

10. The method of claim 9 wherein the drill chuck being secured to said distal end of said housing such that said drill chuck remains secured to said housing when said modular attachment is disconnected from and separated from said handpiece, said drill chuck serving as an adapter to receive a connecting end of an instrument in a distal end thereof.

11. The method of claim 10 further comprising the step of operatively connecting a drivable shaft to said drill chuck, said drivable shaft extending though at least a portion of said housing, said drivable shaft remaining operatively connected to said drill chuck when said modular attachment is disconnected from and separated from said handpiece, and said drivable shaft having a proximal end configured to operatively engage said motor drive shaft.

12. The method of claim 10 further comprising the step of attaching said instrument to said drill chuck.

\* \* \* \* \*